(12) United States Patent
Fukushima et al.

(10) Patent No.: US 6,762,050 B2
(45) Date of Patent: Jul. 13, 2004

(54) MANUFACTURE OF A MICROSENSOR DEVICE AND A METHOD FOR EVALUATING THE FUNCTION OF A LIQUID BY THE USE THEREOF

(75) Inventors: Hitoshi Fukushima, Tsukuba (JP); Tatsuya Shimoda, Nagano-ken (JP); Hywel Morgan, Beith Ayrshire (GB)

(73) Assignees: Seiko Epson Corporation (JP); University Court of the University of Glasgow, Scotland (GB)

( * ) Notice: Subject to any disclaimer, the term of this patent is extended or adjusted under 35 U.S.C. 154(b) by 0 days.

(21) Appl. No.: 09/870,588

(22) Filed: Jun. 1, 2001

(65) Prior Publication Data

US 2001/0044177 A1 Nov. 22, 2001

Related U.S. Application Data

(62) Division of application No. 09/163,199, filed on Sep. 30, 1998.

(30) Foreign Application Priority Data

Sep. 30, 1997 (JP) ............................................. 9-266225

(51) Int. Cl.[7] ......................... C12M 1/36; G01N 27/00; G01N 27/04
(52) U.S. Cl. ............................... 435/287.9; 435/287.1; 435/287.2; 435/286.1; 422/82.01; 422/82.02
(58) Field of Search .......................... 435/287.1, 287.9, 435/287.2, 286.1; 422/50, 56, 58, 100, 82.01

(56) References Cited

U.S. PATENT DOCUMENTS

| | | | |
|---|---|---|---|
| 4,216,245 A | * | 8/1980 | Johnson ..................... 427/2.13 |
| 5,063,081 A | | 11/1991 | Cozzette et al. |
| 5,160,940 A | | 11/1992 | Cassou et al. |
| 5,200,051 A | * | 4/1993 | Cozzette et al. ....... 204/403.07 |
| 5,250,439 A | | 10/1993 | Musho et al. |
| 5,491,097 A | * | 2/1996 | Ribi et al. .................. 436/518 |
| 5,554,339 A | | 9/1996 | Cozzette et al. |
| 5,605,662 A | * | 2/1997 | Heller et al. ............... 422/68.1 |
| 5,671,667 A | | 9/1997 | Simmet |

FOREIGN PATENT DOCUMENTS

| | | |
|---|---|---|
| EP | 0 469 455 A1 | 2/1992 |
| WO | WO8905567 | 6/1989 |
| WO | WO9002829 | 3/1990 |
| WO | WO9108474 | 6/1991 |
| WO | WO9600385 | 1/1996 |

OTHER PUBLICATIONS

Derwent information Ltd., File 351; WPI Accession No. 19962–042844/*199206*; English language abstract.

Plotkin et al., "Convenient Rapid Test for Lead in Blood with use of Disposable Electrodes", Clinical Chemistry, vol. 43,. No. 11, 1997, pp. 2187–2189.

Newman et al., "Ink Jet Printing for the Fabrication of Glucose Biosensors", Analytica Chimica Acta, 1992, pp. 13–17.

(List continued on next page.)

Primary Examiner—Padmashri Ponnaluri
Assistant Examiner—My-Chau T. Tran
(74) Attorney, Agent, or Firm—Harness, Dickey & Pierce, P.L.C.

(57) ABSTRACT

In order to form organic thin films on electrodes, a solution of a material for the organic thin film is accurately printed via an ink-jet onto the surface of microelectrodes as required, thereby producing a high density array of microelectrodes. Further, a solution of a sample substance or a liquid substance to be sensed is ejected into air via an ink-jet nozzle to fall to the surface of organic thin membranes on the microelectrodes so that the sample can be evaluated.

6 Claims, 7 Drawing Sheets

OTHER PUBLICATIONS

O'Donnell–Maloney et al., "Microfabrication and Array Technologies for DNA Sequencing and Diagnostics", Genetic Analysis: Biomolecular Engineering, vol., 13, No. 6, Dec. 1996, pp. 151–157.

A.P. Blanchard et al., High–Density Oligonucleotide Arrays, Biosensors & Bioelctronics, vol., 11, pp. 687–690 (1996).

M. J. Liu et al., Influence of the Doping Conditions on the Surface Energies of Conducting Polymers, Synthetic Metals, 63 pp. 67–71 (1994).

T. F. Otero et al., Conductivity and Capacity of Polythiophene Films: Impedance Study, J. Electroanal. Chem., 244, pp. 311–318 (1988).

* cited by examiner

MANUFACTURE OF A MICROSENSOR DEVICE AND A METHOD FOR EVALUATING THE FUNCTION OF A LIQUID BY THE USE THEREOF

This application is a divisional of U.S. patent application Ser. No. 09/163,199 filed Sep. 30, 1998 and claims priority to Japanese Patent Application No. 9-266,225.

THE FIELD OF THE INVENTION

This invention relates to a device for detecting a trace amount of substance, particularly to a material recognizing device for detecting a bio-molecular or other organic material or the like with a high sensitivity and on a real time basis.

RELATED ART

A biosensor system as a means to monitor a biological function instantaneously has been intensively studied and developed for practical applications heretofore. The basic composition of a biosensor consists of a section for detecting a biological substance and a section for transducing a signal. A biological substance is complexed with the recognizing component of the biosensor, and ensures an ability to detect a bio-molecule, while the signal transducing section transduces a change obtained through the detection of a biological substance into an electric signal. There are many kinds of biological substances which can be detected on the basis of their molecular properties, and they include enzymes, antibodies, binding proteins, lectin, receptors, etc. Examples of biological substances include those that have a molecule recognizing ability and/or catalyzing function. They include enzymes, complex enzyme systems, intracellular organelles, microorganisms, animal cells, plant cells, etc. The catalytic activity of these substances depends on the structure characteristic with enzymes, and can be approximated, in its essence, by the kinetic equation by Michaelis and Menten. Other examples include substances that have a molecule recognizing function, and which forms a stable complex through a biological affinity. They include antibodies, lectin, binding proteins, receptors, etc. The basic designing of a bio-sensor proceeds with attention paid to the above properties. With the recent development of biotechnology, the range of biological substances available for the biosensor has been widened, and thus thermo-resistive enzymes, monoclonal antibodies or the like have come have to be available. To convert the data obtained through molecule recognition into electric signals, physical parameter converting elements such as electrochemical reactions, and an FET, thermistor, piezoelectric element, surface elastic wave element, photodiode, etc. have been utilized.

However, the above-described conventional biosensor devices have technical problems as described below. Firstly, the method for producing a thin film for molecular recognition includes methods based on photoresistance, electrochemical polymerization, manufacture of an LB film, etc. The method based on photoresistance consists of forming a photoresistant film on the entire surface of an ISFET (ion sensitive field effect transistor), exposing only gate parts by lithography, and forming a highly affinitive molecule recognizing film (organic film or biomolecular film) on a gate insulating film. Then, the photoresistant layer is peeled off to leave the molecule recognizing film bonded to gate parts, which serves as a sensor. With this method, however, it is difficult to neatly prepare minute dot electrodes on the molecule recognizing film, and thus an incompletely finished edge of dots results. A reduced yield occurs. Further, waste of materials occurs as a result of lithography. Namely, 99% of photo-setting resin is discarded without being incorporated into actual products, that is, the method causes a wasteful consumption of resources on earth, and contamination of natural environments. This is a big problem. LB technique (Langmuir-Blodgett's technique) is a method whereby a mono-molecular film is formed on the surface of water, and the film is transferred onto the surface of a solid substrate, and for the method to be effective, it is necessary for the mono-molecular layer to have a structure comprising hydrophobic and hydrophilic sections in a balanced state. This method, however, is problematic in that the quality of LB film produced thereby is unsatisfactory in reliability: The film has immeasurable flaws or pores thereupon, and does not allow the formation of an uniform molecular film. Accordingly, with the product manufactured by this method, it is difficult to distinguish a change detected by a molecule recognizing film formed on an electrode from a local change of the electrode.

Furthermore, the sensor film prepared by these methods is a molecule recognizing film composed of one kind of molecule, which recognizes only one kind of biological substance to which the film is sensitive. Still further, it is impossible with these methods to apply different biological substances simultaneously to a plurality of electrodes. Thus, they are problematic in operability and detection efficiency.

With a view to cope with above-described inconveniences, this invention aims at introducing a method for producing a molecule recognizing film distinct from the conventional ones, and further to introduce a method being different, in the manner of detecting biological substances, from the conventional ones.

Namely, one object of this invention is to provide a method for forming, distinct from conventional methods, a molecule recognizing film, uniform and high in quality on a sensor electrode efficiently and in a short time. Further, another object of this invention is to provide a method for forming a plurality of minute sensor electrode dots by said new method for preparing a molecule recognizing film, and for accurately applying a great number of biological samples to be evaluated onto said plural minute sensor electrode dots in a short time and efficiently.

SUMMARY

According to one aspect of this invention, with a sensor device comprising organic thin films formed on an arbitrarily chosen electrode board circuit and electrodes, and a transducing element to transduce information obtained by the organic thin films into electric signals, provided is a method for producing the sensor device wherein a solution of a material of the thin film is accurately printed via an ink-jet nozzle as micro-dots onto the required surface of microelectrodes so that the organic thin films are formed on the electrodes, thereby realizing highly dense microelectrodes.

According to this invention, provided is the sensor device wherein the solution of a material of the thin film comprises an electro-conductive polymer dissolved in a solvent.

According to this invention, provided is the sensor device wherein the solution of a material of the thin film comprises a solution of a silicone-based surface modifying agent, or a mixture thereof with a solvent.

According to this invention, provided is the sensor device wherein the solution of a material of the thin film comprises a mixture resulting from dissolution of a thiol compound in a solvent, and gold thin films are formed on the surface of the electrodes.

According to another aspect of this invention, with said sensor device, provided is a method for evaluating a trace amount of liquid wherein a solution of a sample substance to be sensed is ejected into air as micro-dots via an ink-jet nozzle to fall on the surface of organic thin films of microelectrodes so that the substance is submitted to evaluation.

According to this invention, with the sensor device, provided is a method for evaluating a trace amount of liquid wherein the solution or liquid substance to be sensed and ejected into air as micro-dots via the ink-jet nozzle comprises a protein, DNA, antibody, receptor, lectin, a biomolecule from an animal or plant cell, or a physiologically active substance, or an aqueous solution thereof.

According to another aspect of this invention, provided are the sensor device and the method for evaluating the function of a liquid wherein the electrode or electric circuit is formed on a plastic substrate.

According to another aspect of this invention, provided are the sensor device and the method for evaluating the function of a liquid based on the use of the sensor device wherein the electric circuit is composed of poly-silicon thin film transistors.

DESCRIPTION OF THE EMBODIMENT

One embodiment of the present invention will be described below with reference to attached figures.

Figure 1:
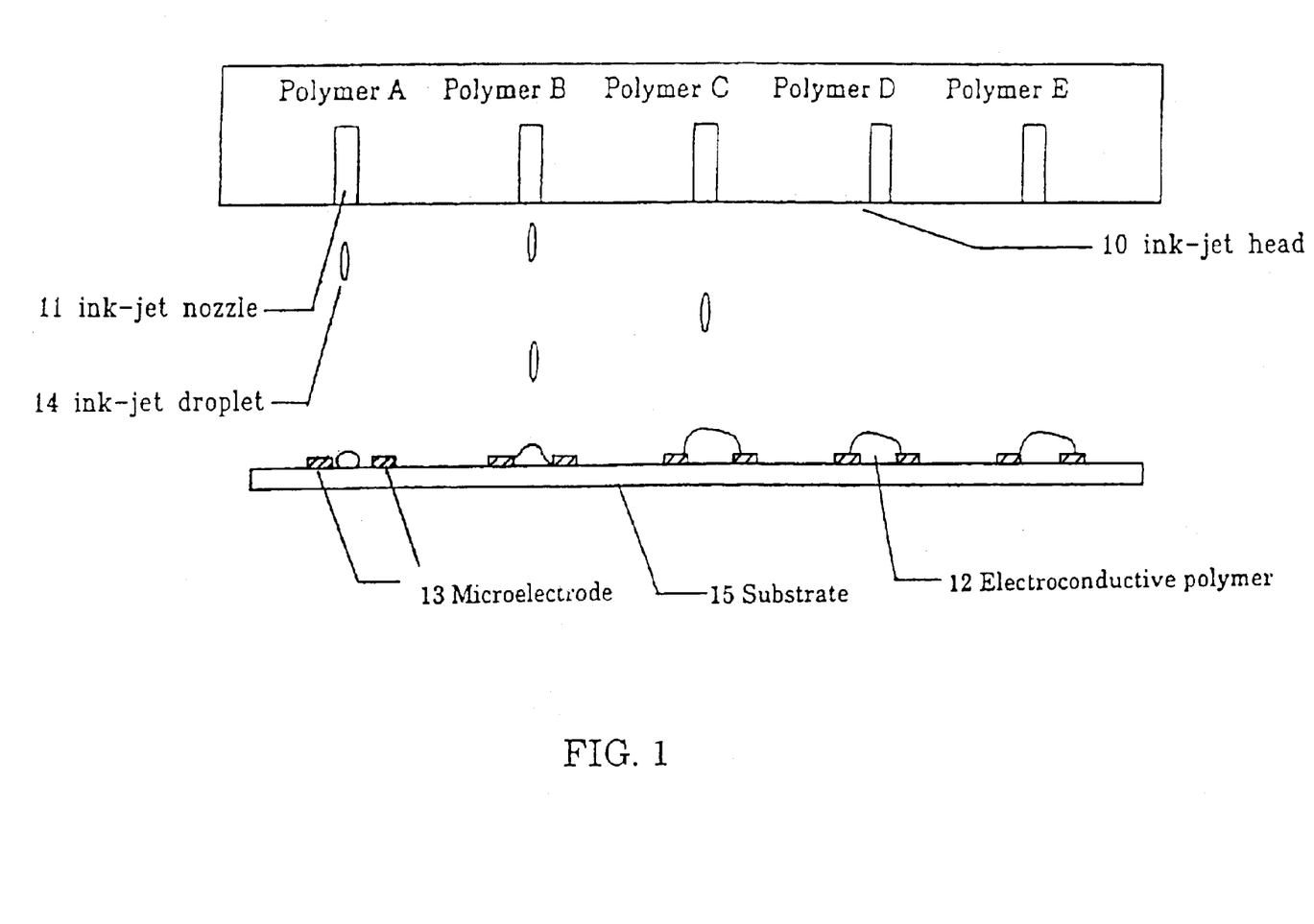
FIG. 1 illustrates how minute electro-conductive polymer electrodes are formed by the method of this invention based on the use of an ink-jet.

FIGS. 1, 2, 3, 4, 5 and 6 show parts of interest to illustrate the structure of a sensor device embodying the present invention. FIG. 1 gives a schematic view of an ink-jet head: 10 stands for an inkjet head; 11 for a head nozzle for ejecting ink droplets; 12 for an electro-conductive polymer applied on the surface of an electrode; 13 for TFT microelectrodes; and 14 for suspended ink droplets ejected via the ink-jet nozzle. The ink-jet head is driven by a piezo-electric element, activating mode, whereby, when an electric signal is delivered from a driving circuit to the piezo-electric element, the piezo-electric element is deformed; a liquid within is pushed out by the deforming pressure; and the liquid is ejected via the nozzle.

Figure 2:
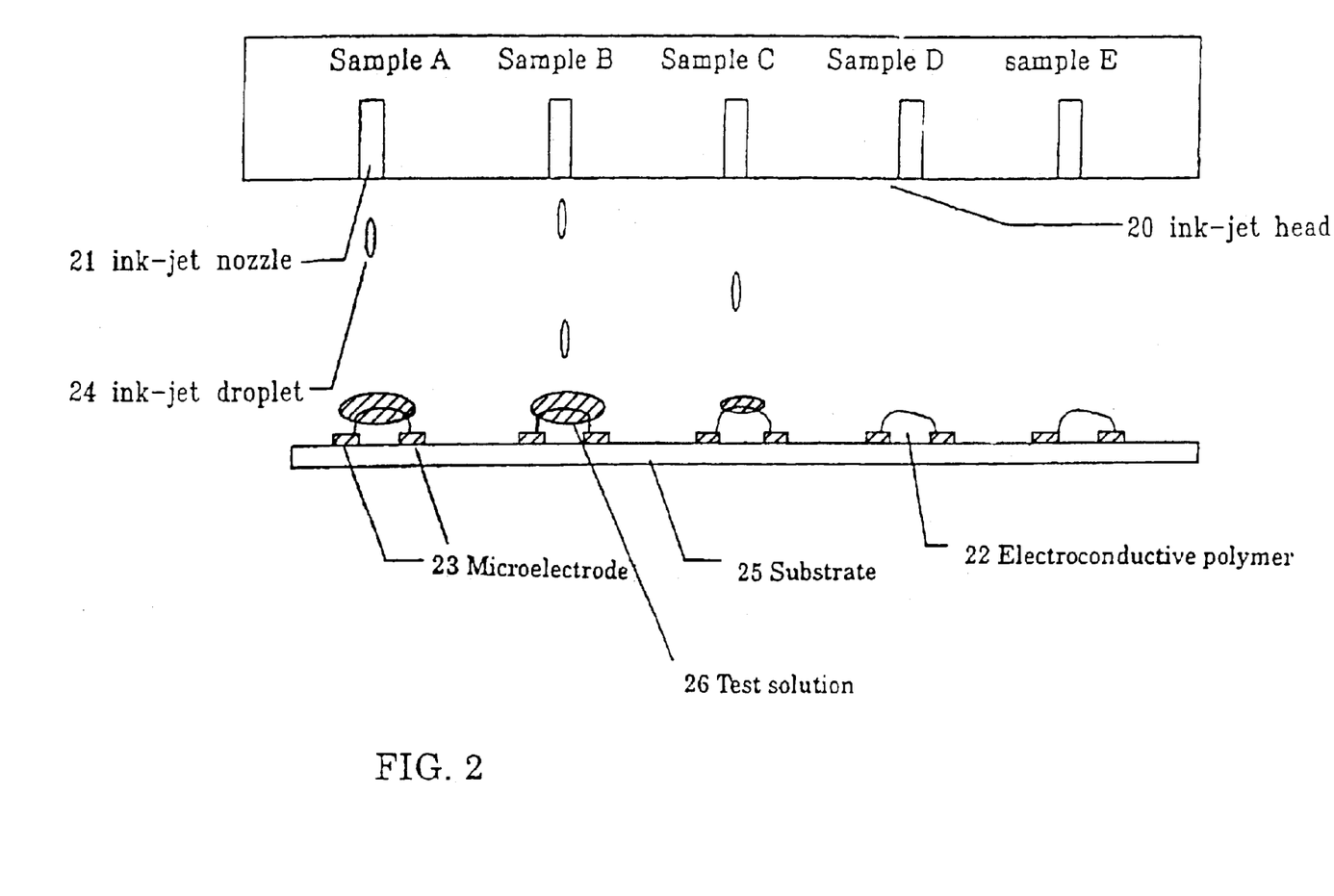
FIG. 2 illustrates how a functional solution sample is analyzed based on the use of an ink-jet.

In this case, the solution of an electro-conductive polymer is ejected via the ink-jet nozzle as micro-dots, and the dots of polymer solution in suspension are allowed to accurately reach the patterned microelectrodes to rest there. The usable electro-conductive polymer, for example, includes polypyrrol, polymethylpyrrol, polythiophene, polymethylthiophene, polyaniline, polyphenylene vinylene, or the like. Preparation of the solution of an electro-conductive polymer requires more or less modifications according to the property of the polymer, because some polymers dissolve in organic solvents while others do not. For an example take polypyrrol as the polymer of illustration. A THF (tetrahydrofuran) solution of 0.30 mmol pyrrol, and another THF solution containing 0.25 mmol phosphor monobutanate as a catalyst and 30 mg of plastisizer are introduced into respective ink-jet tanks by nitrogen purge, and these solutions are ejected onto microelectrodes. Dots composed of two different kinds of solutions are mixed on an electrode to form a mixture there; the mixture is allowed to rest at room temperature for one hour to vaporize the solvent; and a solidified polymer thin film is formed there. Then, the surface of thin membrane is washed with THF or methanol; and residual solvent and unreacted monomers are removed. An electro-conductive polymer soluble in the organic solvent is dissolved in an organic solvent to a concentration at which the solution has a viscosity of 3 cps or less, is then introduced in an ink-jet tank to be ejected. To confer a selective absorbing activity to the electro-conductive polymer, material including a specific type of enzyme molecule or antibody chemically bound to the polymer, artificially synthesized molecule having similar recognizing function to them, or material that a special type of enzyme molecule or antibody is mixed into the electro-conductive polymer, are either dissolved in the solution to give a homogenous solution. Micro dots of various kinds of electro-conductive polymers resulting from polymer/enzyme or polymer/antibody mixtures are ejected via ink-jet nozzles to be printed; the solvent is allowed to vaporize; and a biosensor film results which carries an immeasurable number of sensor dots. Changes in the electric impedance of, or in the electric current through individual microelectrodes covered with respective electro-conductive polymers differ from each other according to the effects exerted by films resulting from agglutination of bio-molecules such as binding proteins, antibodies, DNAs, receptors, etc. adsorbed to the surface, and thus to find what substance is on a given electrode dot is easy. FIG. 2 gives a schematic view of the ink-jet to eject the sample solution onto the surface of individual microelectrodes: 21 stands for the ink-jet head; 22 for nozzles; 23: for microelectrodes; 24 for sample solution; and 25 for suspended droplets of sample solution. In the same manner by which the first molecule recognizing films were formed on the electrodes, micro-dots comprising the sample solution were ejected via the ink-jet nozzle into air and printed on the molecule recognizing films made of an electro-conductive polymer. By virtue of the biomolecular film thus formed on the electro-conductive polymer, changes in electric impedance or in minute electric current through individual electrodes are detected, which allows a quick evaluation/analysis of a huge number of samples For example, production of a patterned array of microelectrodes is possible by ejecting a plurality of electro-conductive polymer solutions via a multi-line head nozzle into air, and thereby forming, for example, ten different kinds of sensor dots each comprising several hundreds line dots.

Figure 3:
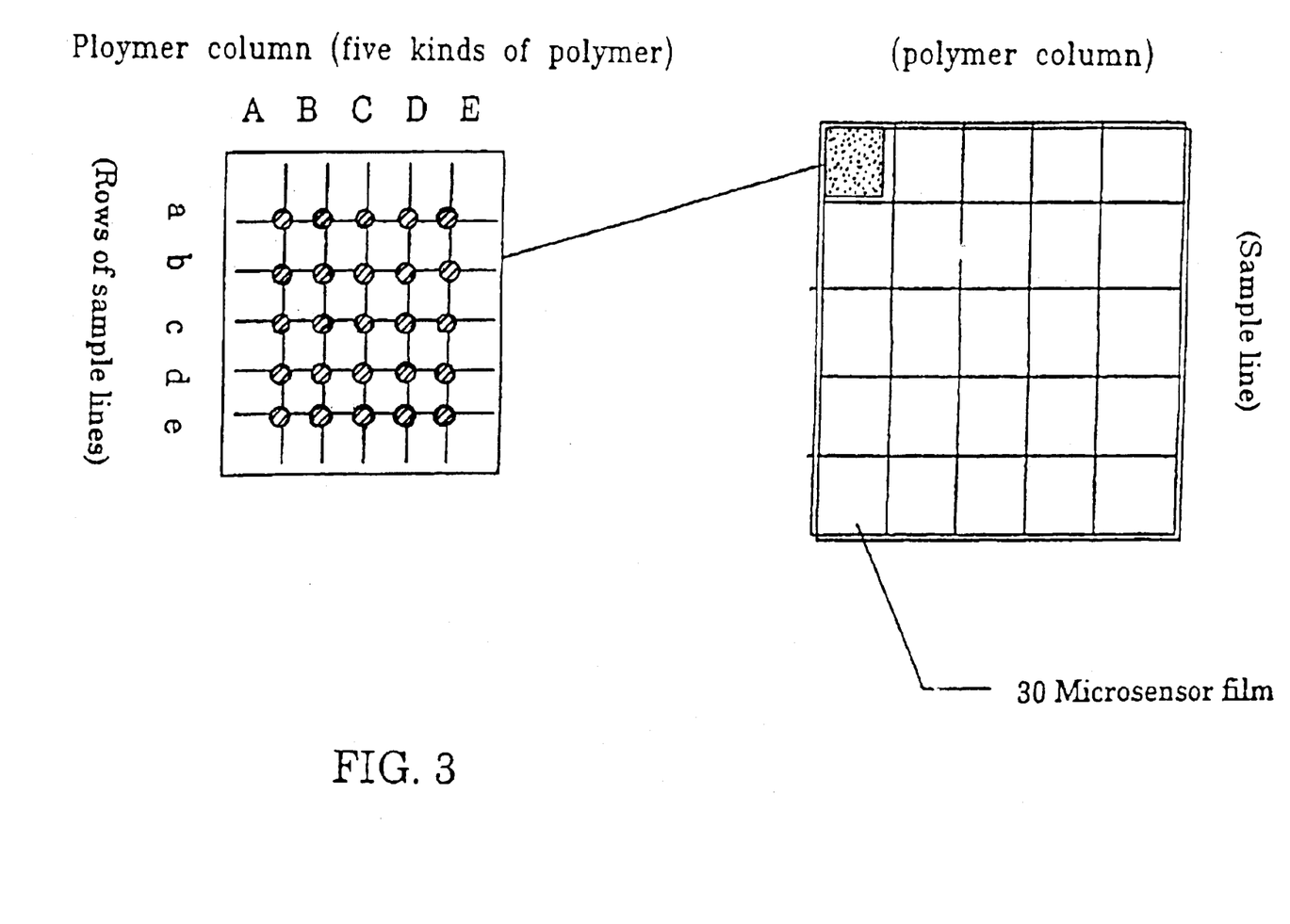
FIG. 3 illustrates how a plurality of functional solution samples are analyzed in a short period on electro-conductive polymer electrodes based on the use of an ink-jet.
Figure 4:
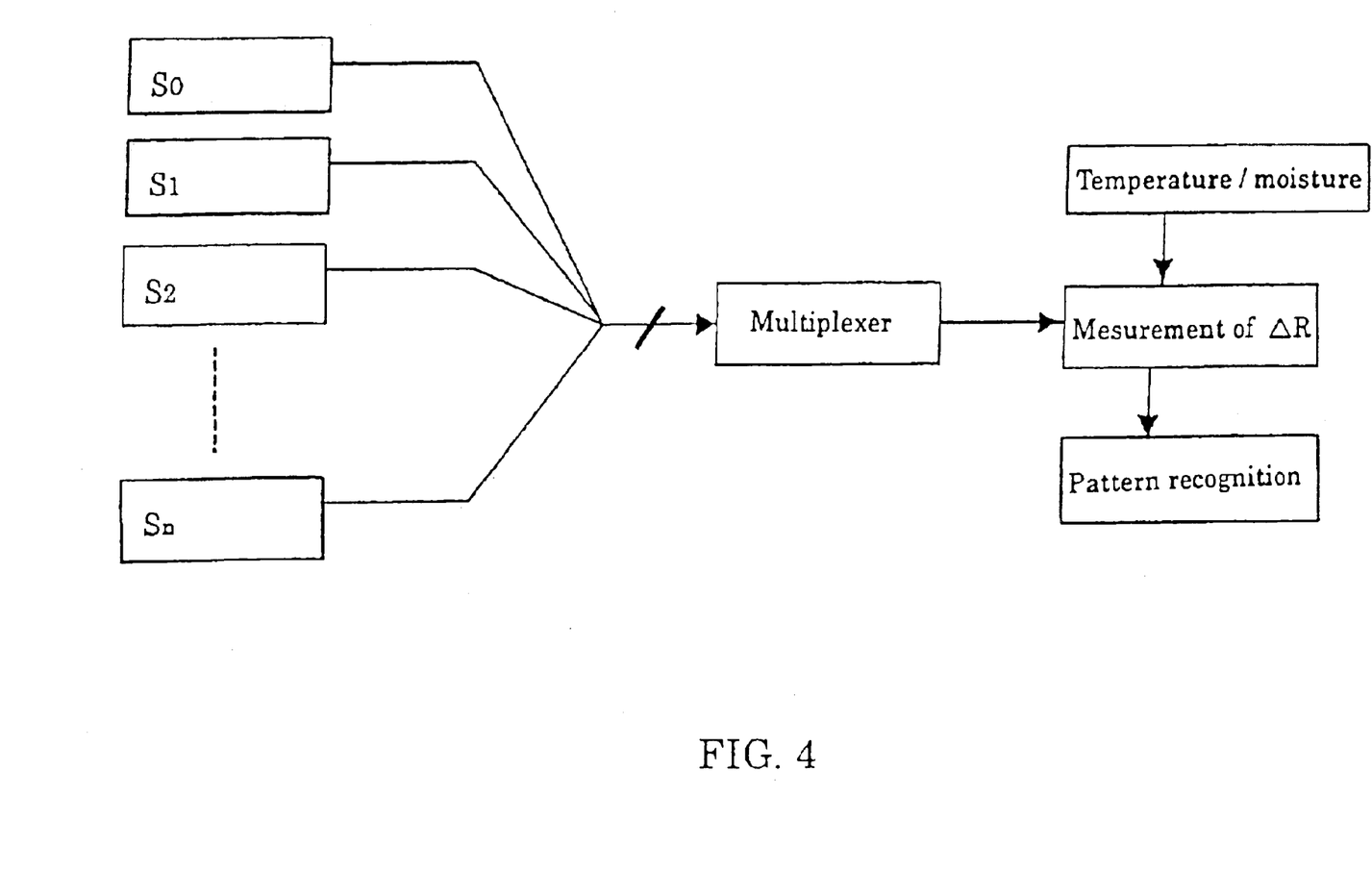
FIG. 4 illustrates the principle underlying the assay method of the microsensor device.

FIG. 3 is a diagram to illustrate how plural lines of dots comprising different electro-conductive polymers are formed on the surface of a substrate like the one as used for the semiconductor circuit board, to form a two-dimensional sensor, and how biological sample dots are formed thereupon to be stabilized there. Assume, as shown in the figure, in a crosswise direction, five different electro-conductive polymers are placed one after another five times in repetition to produce 25 dots in total. These unit arrays are placed in the same manner repetitively in the lengthwise direction to produce a panel of 25 unit arrays which occupies practically the entire surface of substrate. Upon this unit array of microelectrode sensor dots, this time, five different kinds of biological samples are ejected via the ink-jet nozzle in the crosswise direction one after another five times in repetition until 25 micro-dots are suspended in air to fall onto respective electrodes. Then, by monitoring changes in the adsorption of biological material to the electrode, it is possible to assay/evaluate the biochemical characteristics and responsiveness of respective biological samples quickly on a real time basis, and repeatedly and simultaneously. In this particular example, for each of 25 different combinations, data comprising 25 measurements can be obtained. As another example, let's assume a case where an array of micro-dot electrodes comprising ten different kinds of electro-conductive polymers is prepared, and ten different kinds of biological samples are prepared so that they correspond with these dot electrodes. Then, simultaneous measurements based on 100 different combinations become possible. Assume that this forms a unit array, and that the unit arrays are repeated five times to form the same panel as above. Then, it is possible to obtain 25 times repeated measurements for each of 100 different combinations Then, the assay dependent on the use of a sensor device array produced in the manner as described above will be described. FIG. 4 gives a simple block diagram of a circuit responsible for the assay dependent on the use of a resistor sensor array. Principal functions depicted in the figure are roughly presented by a resistor sensor multiplex section, signal processing circuit section and pattern recognizing section. Namely, the function depicted in this figure includes picking up signal from a single channel out of the multi-channel resistors, and processing and recognizing it. Accordingly, it is firstly important to accurately detect a change in impedance.

Figure 5:
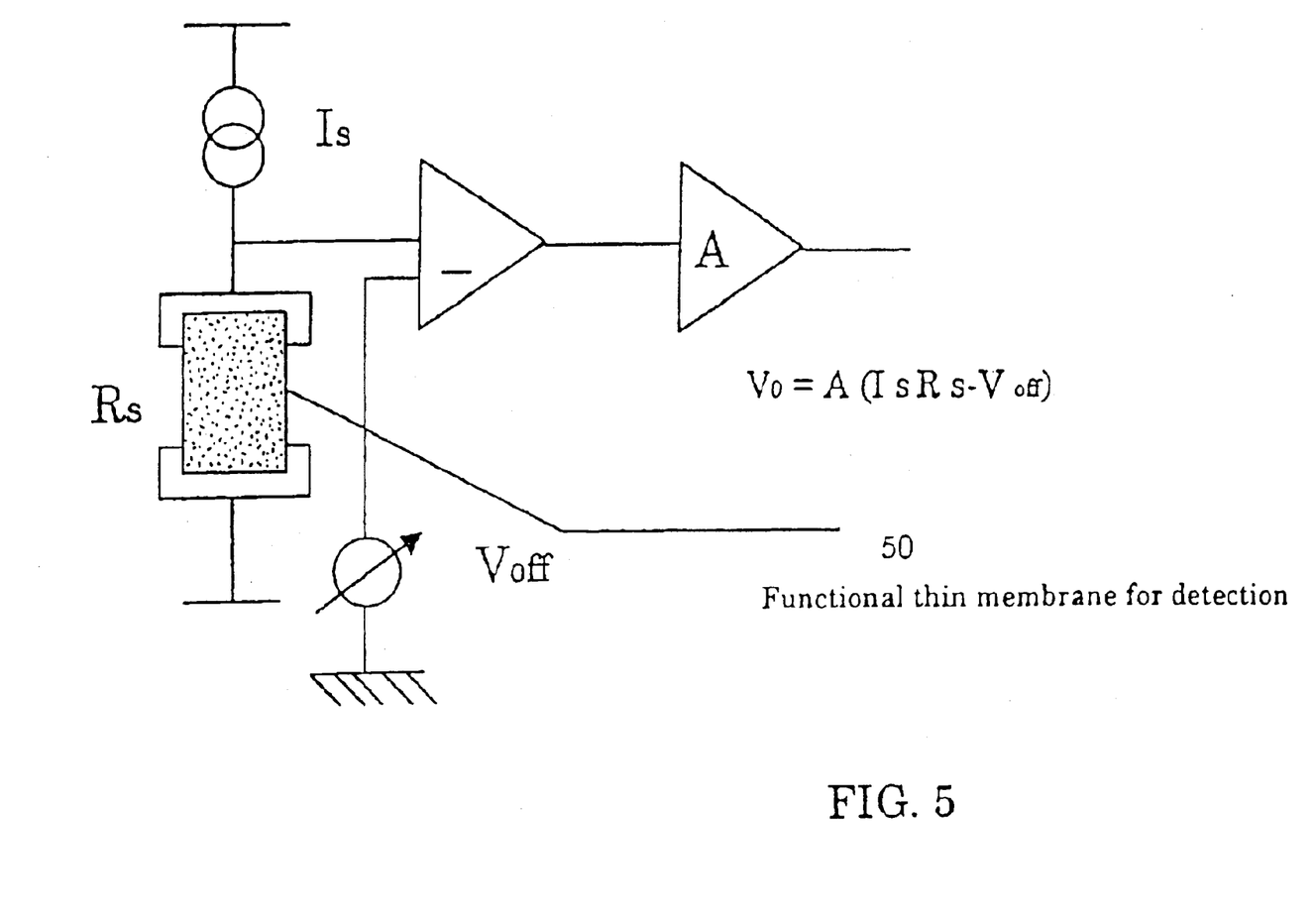
FIG. 5 shows an electronic circuit to collect data for analysis using a microsensor device.

The simplest and most accurate way of determining a resistance includes various bridge methods, but these methods are not suitable for measuring a change in resistance. An alternative method includes a resistance to frequency conversion. This method, however, is disadvantageous in that it is accompanied by noise, and requires a rather longtime for measurement. As one general method for detecting a change in resistance, a circuit working on a voltage mode as shown in FIG. 5 has been known. In this circuit, a specific type of resistance sensor is chosen; a constant current is applied to it; and the voltage across the sensor is monitored. Then, as the voltage varies in proportion to the resistance, it is possible to detect a change in resistance by following a change in voltage. To determine changes in resistance it is advisable to subtract the voltage given as a base to the sensor by means of a differential amplifier, and then to amplify the differential signal with a high-gain amplifier. The sensitivity of the circuit depicted in FIG. 5 is proportional to the gain of amplifier, and is given by the following equation:

$$V_0 = A(I_s R_s - V_{off}),$$

where $(\delta V_0/\delta R_s) = AI_s$.

Figure 6:
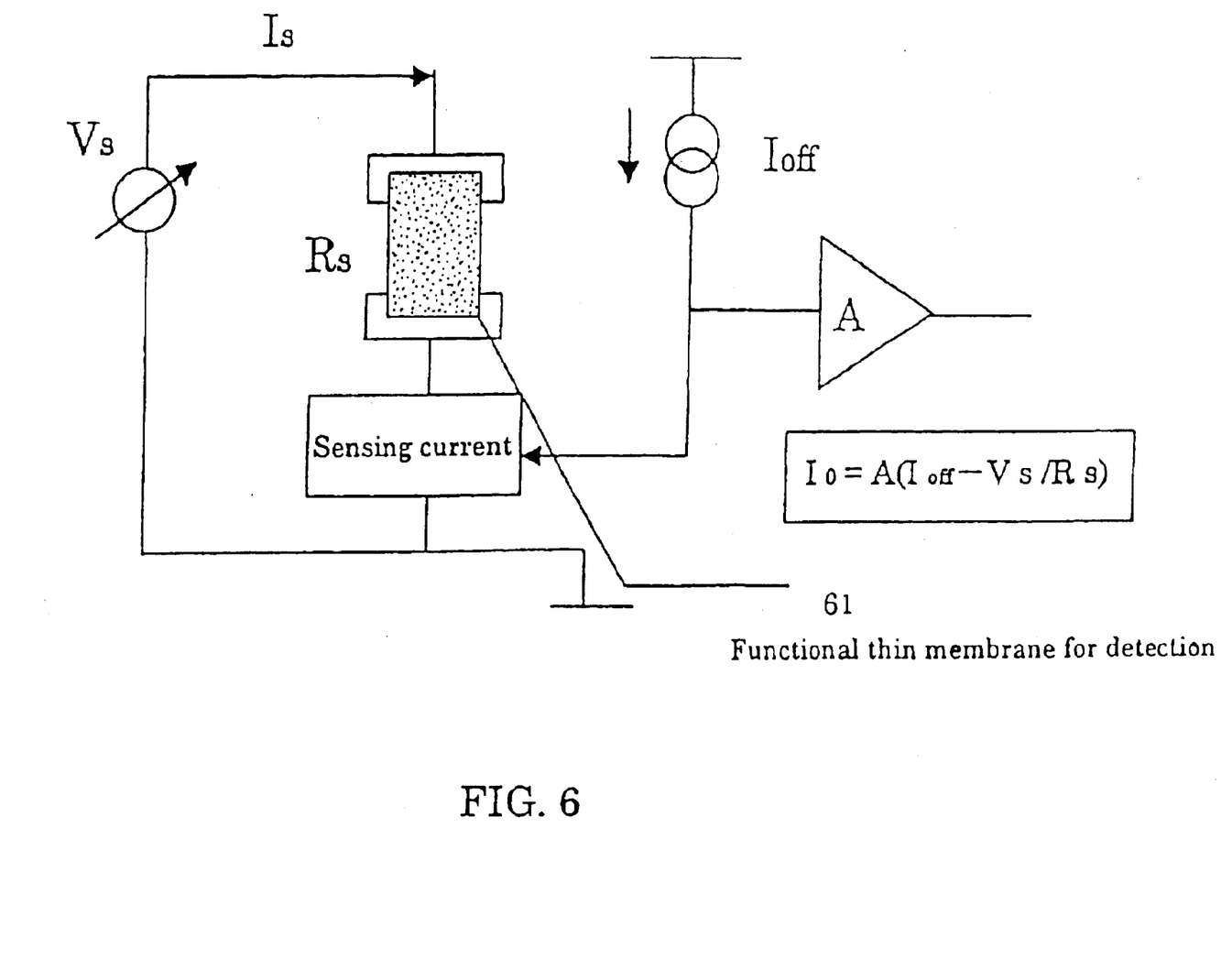
FIG. 6 shows an electronic circuit to collect data for analysis using another microsensor device of this invention.

An alternative method by which to detect a change in resistance includes a method working on a current mode. FIG. 6 gives a circuit diagram of the method. In this figure, a constant voltage is applied to a resistor sensor chosen for this purpose. To measure a change in resistance, a constant current supplied from a source is applied to the sensor as an offset current; differences in current are removed as a signal; and the signal is amplified. The sensitivity of the circuit is proportional to the current gain of amplifier and to the resistance of sensor.

$$I_0 = A(I_{off} V_s/R_s)$$

where $$(\delta I_0/\delta R_s) = A_s/R_s^2 = AI_s/R_s$$

This type of current detection method commands a higher degree of freedom than does the voltage detection method, and thus simplifies the subsequent processing of signals.

The above-described semiconductor circuits are usually constituted of field effect transistors (FET) arranged on a monocrystal silicon substrate. However, because in recent years the function of thin film transistors (TFT) formed on a polycrystal silicon (P—Si) film has made a notable progress, it becomes possible to prepare this type of circuit using polycrystal Si thin film transistors (P—Si TFT). The P—Si TFT has advanced so much that its function is essentially equal to that of monocrystal FET. Further, introduction of the method enabling the manufacture of polysilicon at a low temperature allows the use of a spacious glass substrate. This brings about a great cost-reduction and a method that is suitable for the production of sensor devices like the one described herein.

TFT microelectrodes can be formed not only on a glass substrate but on a thin plastic substrate having a softness and flexibility.

The TFT microelectrodes formed on such substrate can recognize or act upon not only liquid samples, but various gas molecules and volatile substances. Namely, individual volatile molecules are adsorbed to the surface of electro-conductive polymers; the electric resistance of electro-conductive films changes in association; and the change is transformed into an electric signal for detection. For example, the sensor device can be used for the recognition of ethanol, acetone, harmful gases such as chlorine gas, cyanide gas, etc., or vapours of aromatic molecules including perfumes and other odourants. To be precise, this sensor device in film is left in an atmosphere comprising a gas or vapour; the adsorbed gas molecule penetrates through the surface of electro-conductive polymer into its interior; and the entire polymer film changes its volume and/or other property after undergoing expansions/contractions to cause changes in electric resistance of the film. These changes are transformed into electric signals for detection, and fed into a computer, and the information obtained through recognition thereof is available for a quick feedback.

Several sensor arrays formed of field effect TFTs could be used for the simultaneous identification, classification and quantification of odours or other molecules. These sensors could be used in conjunction with other sensors to detect chemicals. The TFT sensors could be integrated onto a single device. Different electro-conductive polymers are placed upon the gates of the TFT sensors using ink-jet technology. In another modification the array of TFTs could be constructed in a pattern to produce a two-dimensional map of the odour response. The output from each TFT would then resemble the output from a pixel of a CCD camera. Different conducting polymers could be deposited onto different regions of the array to produce a device which was specific to a group or class of chemicals, e.g. aromatics. When the molecules bind to or react with the polymer a two-dimensional map corresponding to the particular odours will appear.

The TFT chip should include driving and reading electronics. The information of the odour molecule could be read directly or processed using for example neural networks or classical image processing techniques to identify the odour molecules high sensitively. The density and information of a special type of molecular composition of different odours could thus be obtained.

Figure 7:
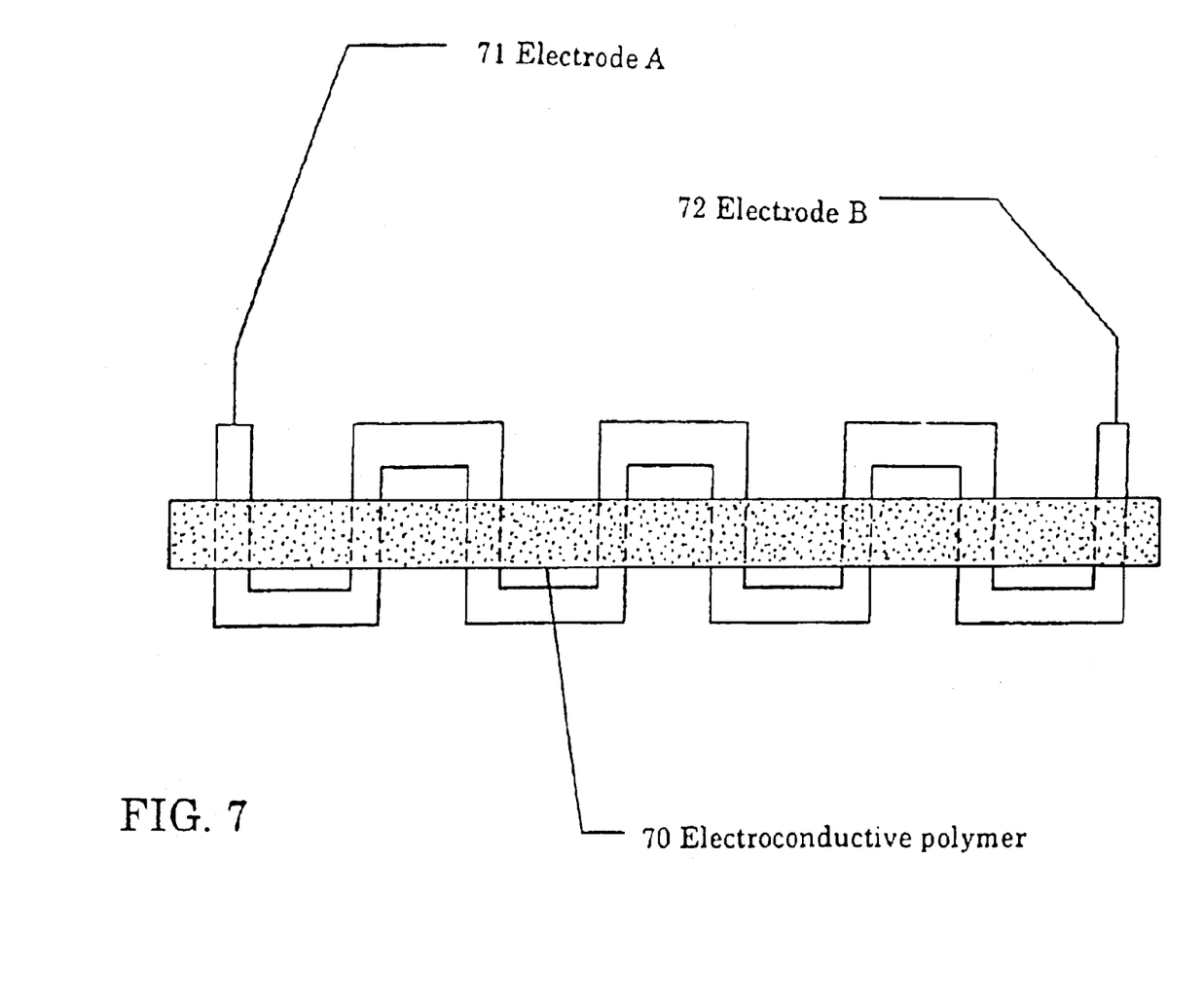
FIG. 7 illustrates how sensor thin membranes having various detection activities are formed on the microelectrodes of a microsensor device.

FIG. 7 is a diagram illustrating how sensor thin films possessed of various detection functions are prepared on the microelectrodes formed on a sensor thin film: 71 stands for an electro-conductive polymer film; and 72 for electrodes A and B. The size of each microelectrode is preferably in the range of 1–100 μm. The sensor is stabilized on the polymer solution electrode which has been ejected via an ink-jet nozzle, and converted to a thin film. A bio-molecule or the like is adsorbed to the surface of this electro-conductive polymer film; and a change in resistance or in current generated as a result of the adsorption is monitored by the above-described detection method.

Alternatively, a silicon-based, functional, surface modifying solution is ejected via an ink-jet nozzle to be applied onto the surface of a microelectrode, to form a silicone-based, functional molecular film there; a bio-molecule is chemically adsorbed to that film to cause thereby electrons within to move towards the surface of electrode; and therewith it is possible to selectively detect the substance adsorbed to the electrode surface. By the use of a device with basically the same in composition with that as depicted in FIG. 7, that is, a device wherein a silicon-based, functional molecular film is formed on an electrode, and an electron-mobile protein molecule such as cytochrome C is bound or adsorbed to that film, it is possible to monitor the adsorption of protein to the surface of electrode by following minute current changes resulting from electron transfer from the protein.

Or, it is possible to plate a gold thin film onto the surface of a microelectrode such that a thiol molecule and gold interact with each other to form a self-organizing agglutination, which results in the formation of a functional, monolayer film. The functional group projecting from the surface of thiol monolayer which has been generated as a result of self-assembly on the gold thin film plated on the microelectrode has a function to selectively recognize a specific bio-molecule or a volatile molecule. For example, as the functional group projecting from the thiol molecule, a biotin derivative may be used. A biotin molecule has a strong binding activity towards a specific binding site of avidin or streptavidin, and its binding constant is about $10^{15}$. This is practically the same as that encountered in a covalent bond. To this biotin molecule film is transferred, for example, a solution of avidin-ferritin binding protein via an inkjet nozzle. Then, avidin and biotin are selectively adsorbed; and the ferritin protein molecule is stabilized on the electrode. The thus selectively adsorbed molecule causes a change in refractive index of the entire molecular film, and that change is captured as a change in dielectric constant of the adsorbing molecular film. Namely, it is possible to convert the microelectrode into a polarized thin film (capacitor), which serves as a sensor.

Advantages

According to this invention, provided is a method by which, in contrast with conventional ones, a molecule recognizing film is efficiently and in a short period formed on a microsensor in a uniform and high quality manner. Further, according to this invention, provided is a method by which to accurately introduce a vast number of biological samples to be evaluated in a short period and efficiently to plural, minute sensor electrode dots which have been prepared according to said method for the formation of a molecule recognizing film.

What we claim are:

1. A sensor device comprising:

a substrate;

resistance sensors formed on the substrate, each of the resistance sensors comprising:

(a) a pair of electrodes; and (b) an electro-conductive polymer deposited on and between the pair of electrodes, wherein the electro-conductive polymer absorbs aromatic molecules and changes an electrical resistance by absorbing the aromatic molecules inside the electro-conducting polymer; and a transducer circuit for transducing the change in the electrical resistance of the electro-conductive polymer into an electric signal, each of the transducer circuits comprising:

(a) a source of electric current electrically connected to the resistance sensor;

(b) a source of an offset voltage;

(c) a differential amplifier electrically connected to the resistance sensor, the differential amplifier outputting a difference between a voltage provided with the resistance sensor and the offset voltage; and (d) a high-gain amplifier that amplifies a voltage output from the differential output, wherein the source of electric current, the source of the offset voltage, the differential amplifier, and the high-gain amplifier comprise thin-film transistors; and the electro-conductive polymer includes at least one of polypyrrol, polymethylpyrrol, polythiophen, polymethylthiophen, polyaniline, and polyphenylene vinylene.

2. The sensor device of claim 1, wherein the electro-conductive polymer is formed from at least one microdot ejected from an ink-jet head.

3. The sensor device of claim 2, wherein at least one micro-dot comprises a dot-shaped area.

4. A sensor device comprising:

a substrate;

resistance sensors formed on the substrate, each of the sensors comprising:

(a) a pair of electrodes; and (b) an electro-conductive polymer deposited on and between the pair of electrodes, wherein the electro-conductive polymer absorbs aromatic molecules and changes an electrical resistance by absorbing the aromatic molecules inside the electro-conductive polymer; and a tranducer circuit for transducing the change in electrical resistance of each of the electro-conductive polymer into an electrical signal, each of the transducer circuits comprising:

(a) a source of voltage that provides a voltage to a resistance sensor;

(b) a source of electric current flowing as an offset current; and (c) a differential amplifier that amplifies a differential current between a current flowing through the resistance sensor and the offset current, wherein the source of voltage, the source of electric current, and the differential amplifier comprise thin-film transistors; and the electro-conductive polymer includes at least one of polypyrrol, polymethylpyrrol, polythiophen, polymethylthiophen, polyaniline, and polyphenylene vinylene.

5. The sensor device of claim 4, further comprising a thiol molecule film formed between the electrodes and the electro-conductive polymer.

6. The sensor device of claim 1, further comprising a thiol molecule film formed between the electrodes and the electro-conductive polymer.

* * * * *